United States Patent [19]

Levy

[11] 4,260,836
[45] Apr. 7, 1981

[54] SOLVENT EXTRACTION OF ALCOHOLS FROM WATER SOLUTIONS WITH FLUOROCARBON SOLVENTS

[76] Inventor: Sidney Levy, 145 W. Cuthbert Blvd., Oaklyn, N.J. 08107

[21] Appl. No.: 110,828

[22] Filed: Jan. 10, 1980

[51] Int. Cl.$^3$ .............................................. C07C 29/86
[52] U.S. Cl. .................................... 568/918; 252/364
[58] Field of Search ......................................... 568/918

[56] References Cited

U.S. PATENT DOCUMENTS

| | | | |
|---|---|---|---|
| 2,582,214 | 1/1952 | Twigg | 568/918 |
| 3,455,664 | 7/1969 | Rosscup et al. | 568/918 |
| 3,705,925 | 12/1972 | Starks et al. | 568/918 |
| 3,793,379 | 2/1974 | Rosscup et al. | 568/918 |

FOREIGN PATENT DOCUMENTS

| | | | |
|---|---|---|---|
| 903609 | 8/1962 | United Kingdom | 568/918 |
| 577201 | 10/1977 | U.S.S.R. | 568/918 |

*Primary Examiner*—Joseph E. Evans

[57] ABSTRACT

Certain fluorocarbon liquid materials are particularly effective solvents for the removal of lower alcohols from aqueous solutions, an extraction process. The fluorocarbons have low heats of vaporization. The specific fluorocarbons recited have boiling points near room temperature which permits the separation of alcohols from the aqueous solutions with much lower energy requirements than required by distillation. The solvent systems are intended for use in fermentation separations such as those recited in my co-pending application Ser. No. 06/076 250 and similar anaerobic and aerobic fermentations to produce alcohols and related fermentation products.

9 Claims, No Drawings

SOLVENT EXTRACTION OF ALCOHOLS FROM WATER SOLUTIONS WITH FLUOROCARBON SOLVENTS

BACKGROUND OF THE INVENTION

In the manufacture of organic chemicals such as ethanol, n-butanol, n-propanol, acetone, and similar materials by fermentation one of the major problems is the recovery of the products from the fermentation liquor. The fermentation liquors contain the product in low concentrations-18% in the case of the yeast fermentation to ethanol, and 2.5% in the case of the Clostridium fermentation for n-butanol—and high energy costs are required to recover the materials in a pure state by conventional processes such as distillation. It is estimated that at least 70% of the energy content of ethanol is required to make it 99.5% pure. In the case of the n-butanol, with its much more dilute liquor, the energy load is much higher. There is current interest in using these alcohols made by the fermentation conversion of biomass materials as fuels. This is not feasible if the separation process uses the amount of energy required by conventional distillation procedures.

There have been other methods proposed for increasing the efficiency of the separation processes. One is by the use of freezing techniques wherein the water is frozen out of the alcohol in a multistage process. While this method is much more energy efficient than distillation, since the heat of fusion of water is substantially less than the heat of vaporization, the process is complicated by the requirements for separating the ice crystals from the liquor at each stage in the process. The capital costs for a freezing separation are substantially higher than for distillation. This essentially negates the thermal advantage.

The method which can be used to substantially improve the efficiency of separation is the use of solvent extraction. This requires the use of solvents with high relative solvency for the alcohol materials so that limited amounts of solvents will be used. In addition, it is necessary that the solvent can be removed from the alcohols with a minimum of energy use. In order to do this by distillation the heat of vaporization and the sensible heat required to evaporate the solvent should be low.

The instant invention uses fluorocarbon solvents which have very high solvency power for alcohols from the $C_2$ to the $C_5$ molecular size, have very low heats of vaporization, and which boil close to ambient temperature. Using these in conjunction with a solvent extraction apparatus as is shown in my co-pending application Ser. No. 06/076 250, that uses a combination of vacuum and pressure to effect the distillation near ambient temperature, will result in a low energy consumption separation of the alcohols and related compounds from the fermentation liquors.

SUMMARY OF THE INVENTION

Accordingly, it is an object of this invention to provide a unique system for the solvent extraction of lower alcohols from dilute aqueous solutions.

It is another object of this invention to provide a process for the extraction of alcohols which uses substantially less energy than conventional distillation processes.

It is a further object of this invention to provide a solvent system which permits the removal of the solvent at ambient temperature with low heat of vaporization requirements to permit efficient low energy cost removal of $C_2$ to $C_6$ alcohols from aqueous solutions.

It is a still further object of this invention to provide a system of fluorocarbon solvents which have the appropriate low energy requirements for distillation and extraction and which are nonflammable materials.

It is yet another object of this invention to provide a system of fluorocarbon solvents which can be distilled from the alcohol fluorocarbon solution by a vacuum-compression cycle at substantially ambient temperature.

It is also an object of this invention to provide a solvent system which is fluorocarbon based that has high chemical stability permitting the continuous recycling of the fluorocarbon solvent without degradation and reducing solvent costs.

It is a final object of this invention to provide a fluorocarbon solvent system which has surface tension and other surface characteristics which permit easy coalescense of the solvent after dispersion in the extraction apparatus avoiding emulsification problems during the extraction.

Table 1 shows the physical properties of the fluorocarbon materials to be used in the instant invention. Table 2 shows the alcohols and a similar chemical on which the solvent fluorocarbons are used.

TABLE 1
PHYSICAL PROPERTIES OF SELECTED FLUOROCARBONS

| | | "FREON-11" $CCl_3F$ | "FREON-12" $CCl_2F_2$ | "FREON-21" $CHCl_2F$ | "FREON-22" $CHClF_2$ | "FREON-114" $CClF_2—CClF_2$ | "FREON-115" $CClF_2—CF_3$ |
|---|---|---|---|---|---|---|---|
| Chemical Formula | | | | | | | |
| Molecular Weight | | 137.38 | 120.93 | 102.93 | 86.48 | 170.93 | 154.48 |
| Boiling Point at 1 atm. | °C. | 23.77 | −29.79 | 8.92 | −40.80 | 3.55 | −38.7 |
| | °F. | 74.78 | −21.62 | 48.06 | −41.44 | 38.39 | −37.7 |
| Freezing Point | °C. | −111 | −158 | −135 | −160 | −94 | −106 |
| | °F. | −168 | −252 | −211 | −256 | −137 | −159 |
| Critical Temperature, | °C. | 198.0 | 112.0 | 178.5 | 96.0 | 145.7 | 80.0 |
| | °F. | 388.4 | 233.6 | 353.3 | 204.8 | 294.3 | 175.9 |
| Critical Pressure | atm. | 43.2 | 40.6 | 51.0 | 48.7 | 32.1 | 30.8 |
| | lbs/sq in abs | 635 | 596.9 | 750 | 716 | 474 | 453 |
| Critical Volume | cc/mol | 247 | 217 | 197 | 164 | 293 | 259 |
| | cu ft/lb | 0.0289 | 0.0287 | 0.0307 | 0.0305 | 0.0275 | 0.0269 |
| Critical Density | g/cc | 0.554 | 0.558 | 0.522 | 0.525 | 0.582 | 0.596 |
| | lbs/cu ft | 34.6 | 34.8 | 32.6 | 32.8 | 36.3 | 37.2 |
| Density, Liquid at 30° C. | g/cc | 1.464 | 1.292 | 1.354 | 1.175 | 1.440 | 1.265 |
| at 86° F. | lbs/cu ft | 91.38 | 80.67 | 84.52 | 73.36 | 89.91 | 78.99 |
| Density, Sat'd Vapor at b.p. | g/l | 5.85 | 6.33 | 4.57 | 4.82 | 7.82 | 8.37 |
| | lbs/cu ft | 0.365 | 0.395 | 0.285 | 0.301 | 0.488 | 0.522 |
| Specific Heat, Liquid (Heat Capacity) | | | | | | | |
| at 30° C. | cal/(g) (°C.) | 0.209 | 0.240 | 0.256 | 0.335 | 0.238 | 0.285 |
| at 86° F. | Btu/(lb) (°F.) | | | | | | |
| Specific Heat, Vapor, at Const. Pressure (Heat Capacity)++ (1 atm.) | | | | | | | |
| at 30° C. | cal/(g) (°C.) | 0.135 | 0.145 | 0.140 | 0.152 | 0.160 | 0.164 |
| at 86° F. | Btu/(lb) (°F.) | | | | | | |
| Specific Heat Ratio, at 30° C. and 1 atm. (Cp/Cv)+ | | 1.136 | 1.137 | 1.175 | 1.184 | 1.088 | 1.091 |
| Heat of Vaporization at b.p. | cal/g | 43.51 | 39.47 | 57.86 | 55.92 | 32.78 | 30.11 |
| | Btu/lb | 78.31 | 71.04 | 104.15 | 100.66 | 59.00 | 54.20 |
| Thermal Conductivity at 30° C. or 86° F. | | | | | | | |
| Liquid | Btu per (hr)(sq ft) (°F. per ft) | 0.0609 | 0.0492 | 0.0697 | 0.0595 | 0.0447 | |
| Vapor (1 atm.) | Btu per (hr)(sq ft) (°F. per ft) | 0.00484 | 0.00557 | 0.00569 | 0.00678 | 0.00646 | |
| Viscosity at 30° C. or 86° F. | | | | | | | |
| Liquid | centipoise | 0.405 | 0.251 | 0.330 | 0.229 | 0.356 | |
| Vapor (1 atm.) | centipoise | 0.0111 | 0.0127 | 0.0116 | 0.0131 | 0.0117 | |
| Surface Tension at 25° C. or 77° F. | dynes/cm | 19 | 9 | 19 | 9 | 13 | |
| Refractive Index of Liq. | $n_D^{26.3°C.}$ | 1.384 | 1.285 | 1.361 | 1.252 | 1.290 | |
| Relative Dielectric Strength at 1 atm and 23° C. (nitrogen = 1) | | 3.1 | 2.4 | 1.3 | 1.3 | 2.8 | 2.8 |
| Dielectric Constant | | | | | | | |
| Liquid | temp. in °C. | 2.28[29] | 2.13[29] | 5.34[28] | 6.11[24] | 2.17[31] | |
| Vapor (0.5 atm.) | temp. in °C. | 1.0019[26] | 1.0016[29] | 1.0035[30] | 1.0035[25.4] | 1.0021[26.8] | 1.0018[27.4] |
| Solubility of "Freon" in Water at 1 atm. and 25° C. (77° F.) | wt. % | 0.11 | 0.028 | 0.95 | 0.30 | 0.013 | 0.006 |
| Solubility of Water in "Freon" | | | | | | | |
| at 30° C. (86° F.) | wt. % | 0.013 | 0.012 | 0.16 | 0.15 | 0.011 | |
| at 0° C. (32° F.) | t.% 0.0036 | 0.0026 | 0.055 | 0.060 | 0.0026 | | |
| Flammability | | nonflammable | nonflammable | nonflammable much less than | nonflammable | nonflammable | nonflammable probably |
| Toxicity | | Group 5A+ | Group 6+ | | Group 5A+ | Group 6+ | |

TABLE 1-continued
PHYSICAL PROPERTIES OF SELECTED FLUOROCARBONS

| Chemical Formula | "FREON-11" $CCl_3F$ | "FREON-12" $CCl_2F_2$ | "FREON-21" $CHCl_2F$ | "FREON-22" $CHClF_2$ | "FREON-114" $CClF-CClF_2$ | "FREON-115" $CClF_2-CF_3$ |
|---|---|---|---|---|---|---|
| | | | Group 4, somewhat more than Group 5+ | | | Group 6 |
| Vapor Pressure at 21° C. PSI absolute | 13 | 83 | 23 | 150 | 28 | 120 |
| Kauri - Butanol Number | 60 | 18 | 102 | 25 | 12 | — |

TABLE 2
PROPERTIES OF LOWER ALCOHOLS AND ACETONE

| | Heat of Combustion cal/gm | Boiling Point °C. | Latent Heat of Evaporation cal/gm |
|---|---|---|---|
| Ethanol | 7120 | 78.5 | 204 |
| n-Propanol | 7500 | 97.2 | 164 |
| n-Butanol | 8630 | 117. | 141 |
| n-Amyl Alcohol | 9019 | 138. | 120 |
| Acetone | 7350 | 56.5 | 124.5 |

DESCRIPTION OF THE PREFERRED EMBODIMENT

The preferred embodiment description will consist of several examples wherein the specific fluorocarbon solvents are used in solvent extractions on fermentation liquors resulting from different fermentation processes.

EXAMPLE 1

The result of the classic Weismann fermentation is a mixture of n-butanol, acetone, and ethanol with the concentrations ranging from 55% to 80% for the butanol, 10% to 30% for the acetone, and 2% to 15% for the ethanol. In general, the acetone is removed from the liquor by evaporation during the fermentation but there is some in the liquor to be extracted.

The specific fluorocarbon solvent which works best with n-butanol is F-11 (monofluoro trichloro methane). From the Table 1 it can be seen that the boiling point is 23.8° C., the heat of vaporization is 43.51 cal/gm, the specific heat is 0.209 cal/gm/°C., and the Kauri-butanol number is 60.

The Kauri-butanol number indicates that the ratio between the concentration of the butanol in water and in the F-11 at room temperature is 1:60. If, by way of example, three parts of F-11 are contacted with ten parts of a 2.5% solution of n-butanol in water, the final concentration of the n-butanol in the F-11 would be 25% and the concentration of n-butanol in the water would be less than 0.4%. Using a countercurrent extraction the residual butanol can be reduced to less than 0.004% by contacting finally with pure F-11.

The F-11 is evaporated by applying a vacuum to the container in which the solution of n-butanol in F-11 is contained. The boiling point at one atmosphere of 23.8° C. is raised by the pressure of the n-butanol, but the material will boil at room temperature at reduced pressures. The heat energy required to do this is supplied from the external environment and the driving force is the pump that creates the vacuum.

One of the main applications of interest for the butanol and other alcohols is use as a fuel. In order to establish a figure of merit for the extraction process the following is used:

$$\frac{\text{extraction}}{\text{efficiency}} = \frac{\text{Heat of combustion} - \text{Heat of extraction}}{\text{Heat of combustion}} \times 100$$

For the extraction of n-butanol using 3 parts by weight of F-11 per part of butanol as hereinbefore described the efficiency would be $$\frac{8630 - 3 \times 43.51}{8630} \times 100 = 98.49\%$$

This value is theoretical but it does represent the efficiency without regeneration, where the heat generated by recompressing the fluid is used to improve the evaporation, in which case less energy would be required. It does not take into account the inefficiency in the system or the fact that the shaft work is used in the compressor. It does show the relatively high thermal efficiency of the extraction process using the F-11 on n-butanol.

EXAMPLE 2

The liquor produced by the yeast fermentation of sugars is generally an 18% solution of ethanol in water. One of the solvents that can be used for the extraction of ethanol from water is F-11 with the same physical properties as were previously recited. The partition coefficient is approximately 8 and the ratio between the concentration of the ethanol in the water phase is one eighth that in the F-11 phase. If nine parts by weight of F-11 are contacted with ten parts by weight of the 18% ethanol water solution the residual concentration of ethanol would be 1.25%. This would be further reduced by contacting the solution with additional pure F-11 to reduce the concentration to less than 0.1%.

The energy extraction efficiency for this process is given by $$\frac{7120 - 9 \times 43.51}{7120} \times 100 = 95.5\%$$

As in the previous example this figure does not take into account the possible use of regenerative heating to reduce the heat energy requirement and increase the efficiency, or the fact that shaft work is required to operate the compressor.

EXAMPLE 3

Others of the commercially available fluorocarbons can be used to separate the alcohols from aqueous solutions. In the case of ethanol, F-21 (monofluoro dichloro methane) would be useful. The Kauri butanol number is 102 and the estimated partition coefficient for ethanol water is 20. The heat of vaporization is 57.86 calories/gram. Starting with an 18% solution of ethanol in water the concentration would be reduced to 1% after ten parts by weight of the solution are contacted with four parts by weight of F-21. After a second stage of contact with pure F-21 the concentration would be reduced to less than 0.05%.

The extraction heat efficiency would be $$\frac{7120 - 4 \times 57.86}{7120} \times 100 = 96.7\%$$

Again, the previously recited limitations with regard to regenerative heating and the use of shaft power apply to this example. It should be further noted that the boiling point of the F-21 is 8.9° C. and that for operation at room temperature of 21° C. the operating pressure of the extraction unit would be 13 psi gauge and the apparatus employed with this solvent would be designed to withstand this pressure.

By comparison of examples 2 and 3 it will be evident that the use of a more polar fluorocarbon solvent is more efficient with ethanol, a more polar alcohol than n-butanol. By the same token less polar F-11 or a mixture of F-11 and F-21 would be more effective on propanol. The combination would have a lower pressure than the F-21 and would be more easily handled.

There are many additional examples of fluorocarbons which can be used in the solvent extraction which are variations of those listed in the table, some of which are not in commercial production and for which there is not data available on the vapor pressure, solvency, and the other data required to determine the efficiency in this type of extraction process or the operating temperature and pressure required. It is intended that such compounds be regarded as embodiments of the present invention if their physical constants fall within the range of those specifically recited. These would be a vapor pressure at room temperature of 150 psi or less, a heat of vaporization of 60 calories per gram or less, a K butanol number of 10 or more and the low surface tension, low viscosity, low water miscibility, low specific heat, and the other handling properties characteristic of the fluorocarbons. As shown in Table 1 numerous combinations of fluorocarbon solvents are possible for the solvent system. The operating conditions with respect to temperature, pressure, and concentrations of the solute alcohol in the initial entry stream, the extract, and the raffinate will vary without departing from the intent and spirit of the invention. These variables would be adjusted to suit the specific requirements of the extraction installation in a manner well known to those skilled in the art. These choices of operating parameters can be made without departing from the spirit and scope of the present invention.

While certain specific embodiments and examples of the invention are hereinbefore recited to illustrate the invention, the scope of the invention is not limited by the specific embodiments only by what is hereinafter claimed.

What is claimed is:

1. The process for separating two to five carbon alcohols in aqueous solution comprising the steps of contacting said aqueous solution with a fluorocarbon solvent system to extract said alcohols from said aqueous phase, separating said alcohol rich fluorocarbon solvent phase from said aqueous phase, removing said fluorocarbon solvent from said solution of said alcohols in said fluorocarbon solvent by vacuum evaporation, compressing and cooling said fluorocarbon vapors to produce liquid fluorocarbon solvent and returning said fluorocarbon solvent to the said extraction process wherein the fluorocarbon solvents comprise singly or mixtures of one and two carbon fluorocarbons that boil at temperatures between $-41°$ C. and $+48°$ C., Have vapor pressures at 21° C. between 10 PSIA and 165 PSIA, have heats of vaporization below 60 calories per gram, have a Kauri butanol number of 10 or greater, have a specific heat below 0.28, have a surface tension below 20 dynes per centimeter, have a viscosity below 0.5 centipoise, have a solubility below 1% in water, and have a solubility below 0.2% of water in the fluorocarbon.

2. The process according to claim 1 wherein the solvent comprise fluorocarbons containing one or two carbon atoms and from one to six fluorine atoms with the remainder being hydrogen, chlorine, and bromine, and admixtures of said fluorocarbons.

3. The process according to claim 1 wherein the fluorocarbons are one or more of the group comprising monochloro difluoro methane, monochloro heptafluoro ethane, dichloro difluoro methane, dichloro tetrafluoro ethane, monofluoro dichloro methane, and monofluoro trichloro methane.

4. The process according to claim 1 wherein the alcohol is butanol and the fluorocarbon solvent is monochloro trifluoro methane.

5. The process according to claim 1 wherein the alcohol is ethanol and the fluorocarbon solvent is monochloro trifluoro methane.

6. The process according to claim 1 wherein the alcohol is propanol and the fluorocarbon solvent is monochloro trifluoro methane.

7. The process according to claim 1 wherein the alcohol is butanol and the fluorocarbon solvent is dichloro tetrafluoro ethane.

8. The process according to claim 1 wherein the alcohol is is ethanol and the fluorocarbon solvent is dichloro tetrafluoro ethane.

9. The process according to claim 1 wherein the alcohol is propanol and the fluorocarbon solvent is dichloro tetrafluoro ethane.

* * * * *